(12) United States Patent
McAnany et al.

(10) Patent No.: US 12,257,342 B2
(45) Date of Patent: *Mar. 25, 2025

(54) PHENYLEPHRINE HYDROCHLORIDE READY-TO-USE SOLUTION

(71) Applicant: Hikma Pharmaceuticals USA Inc., Berkeley Heights, NJ (US)

(72) Inventors: David E. McAnany, Berkeley Heights, NJ (US); Michael G. Parker, Berkeley Heights, NJ (US); Sarah D. Mccue, Berkeley Heights, NJ (US)

(73) Assignee: Hikma Pharmaceuticals USA Inc., Berkeley Heights, NJ (US)

( * ) Notice: Subject to any disclaimer, the term of this patent is extended or adjusted under 35 U.S.C. 154(b) by 273 days.

This patent is subject to a terminal disclaimer.

(21) Appl. No.: 17/941,640

(22) Filed: Sep. 9, 2022

(65) Prior Publication Data
US 2023/0014425 A1    Jan. 19, 2023

Related U.S. Application Data

(63) Continuation of application No. 17/495,548, filed on Oct. 6, 2021, now Pat. No. 11,471,400, which is a
(Continued)

(51) Int. Cl.
*A61K 9/00* (2006.01)
*A61J 1/06* (2006.01)
(Continued)

(52) U.S. Cl.
CPC ............ *A61K 9/0019* (2013.01); *A61J 1/06* (2013.01); *A61K 9/08* (2013.01); *A61K 31/137* (2013.01);
(Continued)

(58) Field of Classification Search
CPC ........... A61P 11/00; A61P 13/12; A61P 17/00; A61P 1/16; A61P 1/18; A61P 27/02; A61P 37/06; A61P 9/00; A61P 19/10; A61P 25/00; A61P 25/04; A61P 37/00; A61P 3/00; A61P 3/04; A61P 3/06; A61P 3/10; A61P 9/12; A61P 11/02; A61P 11/04; A61P 11/06; A61P 11/14; A61P 11/16; A61P 15/00; A61P 17/02; A61P 17/04; A61P 17/06; A61P 17/08; A61P 17/10; A61P 17/14; A61P 19/00; A61P 19/02; A61P 19/04; A61P 19/08; A61P 1/02; A61P 1/04; A61P 1/14; A61P 21/00; A61P 21/04; A61P 25/02; A61P 25/14; A61P 25/18; A61P 25/20; A61P 27/06; A61P 27/12; A61P 27/14; A61P 27/16; A61P 29/00; A61P 29/02; A61P 31/04; A61P 31/06; A61P 31/18; A61P 31/20; A61P 31/22; A61P 33/02; A61P 35/02; A61P 37/08; A61P 39/02; A61P 3/02; A61P 5/00; A61P 5/14; A61P 5/38; A61P 7/00; A61P 7/04; A61P 7/06; A61P 7/10; A61P 9/10; A61P 9/14; C07D 405/14; C07D 409/14; C07D 417/14; C07D 401/04; C07D 401/14; C07D 471/04; C07D 401/06; C07D 405/04; C07D 409/10; C07D 519/00; C07D 231/56; C07D 235/18; C07D 403/04; C07D 403/14; C07D 405/06; C07D 413/14; C07D 417/06; C07D 471/08; C07D 491/04; C07D 235/26; C07D 237/28; C07D 263/24; C07D 263/32; C07D 309/32; C07D 401/12; C07D 403/06; C07D 403/12; C07D 405/10; C07D 407/10;
(Continued)

(56) References Cited

U.S. PATENT DOCUMENTS

| 5,599,846 A | 2/1997 | Chopdekar et al. |
| 5,942,241 A | 8/1999 | Chasin et al. |

(Continued)

FOREIGN PATENT DOCUMENTS

| CN | 102525893 B | 11/2013 |
| EP | 2046289 B1 | 1/2014 |

(Continued)

OTHER PUBLICATIONS

Drug label, Phenylephrine HCL—phenylephrine hydrochloride injection, solution, Cantrell Drug Company Dhenylephrine HCl 50 mcg/ml in 0.9% Sodium Chloride 20 ml Syringe. Dated Oct. 2012; retrieved from the Internet I \ug_7, 2017. (https://dailymed .nlm .nih.gov/dailymed/archives/fdaDrugInfo.cfm?archiveid=91184).

(Continued)

*Primary Examiner* — Savitha M Rao
(74) *Attorney, Agent, or Firm* — Fox Rothschild LLP

(57) ABSTRACT

This invention relates to a dilute, ready-to-use solution of phenylephrine hydrochloride having improved stability and utility. In a particular embodiment, the formulation consists of an injectable form of phenylephrine hydrochloride with edetate disodium chelating agent in place of any sodium metabisulfite antioxidants to improve the solution's ability to remain stable and active in a dilute state after prolonged storage. This invention also relates to a form for injection of the solution that includes packaging the solution in a single-use container, as well as a form for containing the ready-to-use solution in a sterile, sealed container. Lastly this invention relates to methods of making the injectable solution for use in a single-use container, as well as for containment in a sterile, sealed container.

21 Claims, No Drawings

Related U.S. Application Data continuation of application No. 15/230,352, filed on Aug. 5, 2016, now Pat. No. 11,213,480.

(60) Provisional application No. 62/202,146, filed on Aug. 6, 2015.

(51) Int. Cl.

| | | |
|---|---|---|
| *A61K 9/08* | (2006.01) | |
| *A61K 31/137* | (2006.01) | |
| *A61K 47/02* | (2006.01) | |
| *A61K 47/10* | (2017.01) | |
| *A61K 47/12* | (2006.01) | |
| *A61K 47/18* | (2017.01) | |
| *B65B 3/00* | (2006.01) | |
| *B65B 7/16* | (2006.01) | |
| *B65B 55/06* | (2006.01) | |

(52) U.S. Cl.
CPC .............. *A61K 47/02* (2013.01); *A61K 47/10* (2013.01); *A61K 47/12* (2013.01); *A61K 47/183* (2013.01); *B65B 3/003* (2013.01); *B65B 7/16* (2013.01); *B65B 55/06* (2013.01)

(58) Field of Classification Search
CPC .. C07D 413/04; C07D 471/10; C07D 487/10; C07D 491/107; C07D 493/04; C07D 498/04

See application file for complete search history.

(56) References Cited

U.S. PATENT DOCUMENTS

| | | | |
|---|---|---|---|
| 5,980,882 | A | 11/1999 | Eichman |
| 6,093,181 | A | 7/2000 | Place et al. |
| 7,115,275 | B2 | 10/2006 | Clarot et al. |
| 8,603,523 | B2 | 12/2013 | Atkinson |
| 8,628,805 | B2 | 1/2014 | Baillie et al. |
| 8,859,623 | B1 | 10/2014 | Witham et al. |
| 2007/0104791 | A1 | 5/2007 | Popov et al. |
| 2007/0249566 | A1 | 10/2007 | Martin et al. |
| 2008/0008762 | A1 | 1/2008 | Robinson et al. |
| 2011/0104273 | A1 | 5/2011 | Hou |
| 2013/0023575 | A1 | 1/2013 | Hosseini et al. |
| 2014/0235691 | A1 | 8/2014 | Demopulos et al. |
| 2014/0329874 | A1 | 11/2014 | Gil et al. |
| 2015/0057325 | A1 | 2/2015 | Johansson et al. |

FOREIGN PATENT DOCUMENTS

| | | |
|---|---|---|
| WO | 00/48636 A1 | 8/2000 |
| WO | 2004087071 A2 | 10/2004 |
| WO | 2006/041942 A2 | 4/2006 |
| WO | 2007/025286 A2 | 3/2007 |
| WO | 2009/033053 A1 | 3/2009 |
| WO | 2014/052792 A1 | 4/2014 |

OTHER PUBLICATIONS

Drug label, Phenylephrine HCL—phenylephrine hydrochloride injection, solution, Cantrell Drug Company_Dhenylephrine HCI 80 mcg/ml in 0.9% Sodium Chloride 10 ml Syringe. Dated May 2014; retrieved from the Internet I \lug_7, 2017. (https://dailymed .nlm . nih.gov/dailymed/archives/fdaDrugInfo.cfm?archiveid= 140941.

Drug label, Phenylephrine HCL—phenylephrine hydrochloride injection, solution, Cantrell Drug Company_Dhenylephrine HCI 80 mcg/ml in 0.9% Sodium Chloride 10 ml Syringe. Dated Aug. 2012; retrieved from the Internet I \ug_7, 2017. (https://dailymed.nlm.nih. gov/dailymed/archives/fdaDrugInfo.cfm?archiveid=87323).

Drug Label, Childrens Robitussin Cough and Cold CF—dextromethorphan hydrobromide, guaifenesin, and : 1henylephrine hydrochloride liquid, Richmond Division of Wyeth. Dated Sep. 2012; retrieved from the Internet Aug. 7, 2017. (https:// dailymed .nlm .nih.gov/dailymed/archives/fdaDrugInfo.cfm?archiveid= 89713).

Drug label, Despec OM Syrup—dextromethorphan hydrobromide, guaifenesin and phenylephrine hydrochloride syrup, International Ethical Laboratories, Inc. Dated May 2012; retrieved from the Internet Aug. 7, 2017. https://dailymed.nlm.nih.gov/dailymed/archives/fdaDrugInfo.cfm?archiveid=88437).

Hovorka, et al., "Oxidative Degradation of Pharmaceuticals: Theory, Mechanisms and Inhibition", Journal of Pharmaceutical Sciences (2001); vol. 90:3; pp. 253-269.

Label, PHENYLephrine HCI 80 mcg/mL PF in 0.9% Sodium Chloride 10 mL, Cantrell Drug Company. (date unknown, but believed to be available prior to the filing date of this application).

PHENYLEPHRINE HYDROCHLORIDE READY-TO-USE SOLUTION

This application is a continuation of U.S. application Ser. No. 17/495,548, filed Oct. 6, 2021, which is a continuation of U.S. application Ser. No. 15/230,352, filed Aug. 5, 2016, which claims the benefit of priority to U.S. Application No. 62/202,146 filed Aug. 6, 2015, the entire content of each application is expressly incorporated herein by reference in its entirety.

FIELD OF THE INVENTION

The present invention relates to stable, preservative-free, ready-to-use solutions of phenylephrine hydrochloride that are available in single or limited use quantities.

BACKGROUND

Phenylephrine hydrochloride is an α–1 adrenergic receptor used in injection form to increase blood pressure in adults with clinically important hypotension resulting primarily from vasodilation, in such settings as septic shock or anesthesia. Chemically, phenylephrine hydrochloride is (–)-m-Hydroxy-α-[(methylamino)methyl]benzyl alcohol hydrochloride and has the following structural formula:

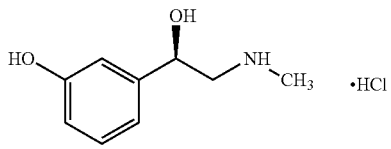

Phenylephrine hydrochloride is very soluble in water, freely soluble in ethanol, and insoluble in chloroform and ethyl ether. It is also sensitive to light.

Phenylephrine is an α–1 adrenergic receptor agonist. Following parenteral administration, increases in systolic blood pressure, diastolic blood pressure, mean arterial blood pressure, and total peripheral vascular resistance are observed. The onset of blood pressure increase following an intravenous bolus phenylephrine hydrochloride administration is rapid and the effect may persist for up to 20 minutes.

Phenylephrine hydrochloride in injection form is approved for marketing in the United States as a 10 mg/mL concentrated solution. At this concentration, phenylephrine hydrochloride must be diluted before administration as a bolus intravenous infusion or a continuous intravenous infusion. The usual dosing recommendation for phenylephrine hydrochloride is 0.05 to 0.10 mg. For bolus intravenous administration, 1 mL of a 10 mg/mL concentration of phenylephrine injection must be diluted with 99 mL of 5% Dextrose Injection, USP or 0.9% Sodium Chloride Injection, USP, yielding a final concentration of 0.10 mg/mL. For continuous intravenous infusion, 1 mL of a 10 mg/mL solution of phenylephrine hydrochloride injection must be added to 500 mL of 5% Dextrose Injection, USP or 0.9% Sodium Chloride Injection, USP, providing a final concentration of 0.02 mg/mL. The need to dilute the solution is inconvenient and introduces opportunities for calculation and compounding confusion that can lead to dosing errors including over dosage. Dilution can also lead to concerns for the stability and introduces opportunities for contamination and the need to preserve the solution from microorganisms. Once diluted, the solution should not be held for more than 4 hours at room temperature or 24 hours under refrigerated conditions.

Currently approved solutions of phenylephrine hydrochloride injection are based on the following formulation: phenylephrine hydrochloride 10 mg/mL; sodium chloride 3.5 mg/mL; sodium citrate dehydrate 4 mg/mL; citric acid monohydrate 1 mg/mL; and sodium metabisulfite 2 mg/mL; all in water for injection (WFI). The sodium metabisulfite is added as an antioxidant. The pH may be adjusted in the range of 3 to 6.5 with sodium hydroxide and/or hydrochloric acid, or another pH buffering agent, if necessary.

Phenylephrine is susceptible to auto-oxidation, an oxidation reaction that occurs spontaneously under mild conditions. Most auto-oxidation reactions are free radical type reactions with organic peroxides often being the intermediates of the final products. Oxygen is itself a di-radical, and radicals are formed by thermal or photolytic homolytic cleavage of covalent bonds or by redox processes involving one-electron transfer steps (Kenneth A. Connors, Gordon L. Amidon & Lloyd Kennon, "Chemical Stability of Pharmaceuticals, A Handbook for Pharmacists", John Wiley & Sons, New York, September 1978).

Auto-oxidation is a chain process that occurs in three sequential steps: initiation, propagation and termination. Initiation requires oxidation by molecular oxygen or by reaction of the drug with other endogenous chain-initiating radicals. The induction period involves generation of substrate radicals that are necessary for propagating the chain. In a pharmaceutical formulation, chain-initiating radicals can be generated by exposing the formulation to light, heat and catalytic levels of redox-active transition metals (Suzan W. Hovorka & Christian Schoneich, "Oxidative Degradation of Pharmaceuticals: Theory, Mechanisms and Inhibition", Journal of Pharmaceutical Sciences, Vol. 90, 3, March 2001). Termination reactions break the chain and create nonreactive products. Termination reactions typically involve free-radical inhibitors such as sulfite, thiourea, aromatic amines, and phenols (Connors, supra.).

Antioxidants can function by being more readily oxidized than the agents to which they are added to protect. Thus, in a pharmaceutical formulation, the antioxidants can consume essentially all of the oxygen present and thereby protect the drug. Antioxidants can also function by inhibiting free radicals by donating an H+ or an electron to break the chain reaction of oxidation (Connors, supra.).

In the course of developing dilute, stable ready-to-use ("RTU") formulations of phenylephrine hydrochloride, it has been found that conventional anti-oxidants, such as sodium metabisulfite—which stabilize the formulation when used in the prior art concentrated formulations—do not protect the more dilute RTU formulations from oxidation but actually destabilize the formulation. For example, simply diluting a currently marketed sodium metabisulfite containing 10 mg/mL phenylephrine hydrochloride solution to a ready-to-use concentration does not result in a sufficiently stable formulation.

A number of prior art references disclose formulations using phenylephrine hydrochloride. U.S. Pat. No. 8,603,523 B2 (523 patent), discloses a phenylephrine hydrochloride based formulation for treating upper respiratory mucosal congestion. The solution comprises 10 mg phenylephrine hydrochloride, 2.50 mg loratadine, 180.40 mg lactose, 140.00 mg maize starch, 10.365 mg pregelatinised starch, 0.20 mg lake of quinoline yellow, 0.40 mg sodium metabisulfite, 0.14 mg edetate disodium 3.00 mg talc and 3.00 mg magnesium stearate. The '523 patent illustrates the conventional use of sodium metabisulfite as an antioxidant.

US publication US 2007/0249566 A1 (566 application), discloses a phenylephrine solution that includes a chelating agent of edetate disodium. The solution has a pH range of approximately 2 to 4.75, with a preferred range from 3 to 4.5 and is substantially free of aldehydes. The solutions typically contain one or more solvents selected from water, propylene glycol, ethanol glycerol, sorbitol, and mixtures thereof, and an additional pharmaceutical active selected from the group consisting of antitussives, antihistamines, non-sedating antihistamines, decongestants, expectorants, analgesics, antipyretic anti-inflammatory agents, local anesthetics, anti-inflammatory agents, demulcents, and mixtures thereof. The solutions also optionally contain a metal chelator or a reducing agent.

US publication US 2014/0235691 A1 (691 application), discloses a sterile, preservative-free and antioxidant-free liquid formulation of a mydriatic agent, phenylephrine, and an anti-inflammatory agent, ketorolac, for injection. The formulation incorporates a buffer system to maintain the pH between 5.8 and 6.8 with 6.3 as the pH of the solution in its preferred embodiment. Additionally, the '691 application teaches that there is no need for any inclusion of edetate disodium (EDTA) in its preservative-free formulation. The '691 application provided examples suggesting that EDTA does not provide additional formulation stability when included as a preservative in studies at the preferred pH, 6.3. Accordingly, based on those studies, the '691 application disclaims the presence of EDTA.

U.S. Pat. No. 5,980,882 ('882 patent) discloses a pharmaceutical composition comprising a drug resin complex and an EDTA chelating agent to stabilize the complex. The '882 patent provides a method of using chelating agents to stabilize drugs which have been taken up by resins and, in particular, ion exchange resins. The drugs are not in solution, but rather present in the form of a drug-resin complex. The drug may be any of a wide variety of drugs suitable for the formation of a drug-resin complex and subject to degradation after complexation. The ion exchange resin may be any non-toxic ion exchange resin. The chelating agent, which may be EDTA or a salt of EDTA, may be added during the formation of the complex, after its formation, or at any time during the process. The stabilization is effective either when the complex is dry or when the complex is suspended in water. The complex may be coated or uncoated as necessary to obtain a desirable dissolution profile. Solvating agents may be used in the process to prevent the resin particles from breaking and to aid in the application of coatings. Also, resins such as amphoteric resins and other neutral resins may also be used.

In view of the foregoing, therefore, there remains a need for a stable, ready to use phenylephrine formulation that is available in single or limited use quantities. The present invention now satisfies that need.

SUMMARY OF THE INVENTION

The present invention now provides a ready-to-use, injectable formulation of phenylephrine hydrochloride, at concentrations that can be used without further dilution, and that remains stable and active after prolonged storage. These ready-to-use formulations avoid the drawbacks associated with prior art phenylephrine solutions which require multiple dilutions prior to use, thereby increasing the overall cost and risks of contamination, over dosage and calculation errors.

In particular, the present invention relates to a stable, ready-to-use sterile injection solution of phenylephrine hydrochloride consisting essentially of from about 0.05 mg/mL to about 0.15 mg/mL phenylephrine hydrochloride as the sole active agent in the solution; from about 3 mg/mL to about 4 mg/mL of sodium chloride; from about 0.1 mg/mL to about 0.3 mg/mL of edetate disodium (EDTA); and water. Advantageously, the solution has a pH between 3 and 6.5 and exhibits 0.2% or less of phenylephrine impurities after exposure to a temperature of 40° C. for a period of 6 months.

The solution is free of bisulfites or other antioxidants and further consists essentially of one or more of a preservative, a buffer and/or a pH adjustor. When present, the preferred preservative is benzyl alcohol. When the buffer is present, it is preferably a citrate buffering system for assisting in maintaining the pH of the solution. And if necessary, the pH can be adjusted with hydrochloric acid, sodium hydroxide or both. A preferred pH is between 5 and 5.3. Also the solution preferably exhibits about 0.1% or less of phenylephrine impurities after exposure to a temperature of 40° C. for a period of 6 months.

Another embodiment of the invention relates to a ready-to-use sterile injection solution of phenylephrine hydrochloride consisting of from about 0.05 mg/mL to about 0.15 mg/mL phenylephrine hydrochloride as the sole active agent in the solution; from about 3 mg/mL to about 4 mg/mL of sodium chloride; from about 0.1 mg/mL to about 0.3 mg/mL of edetate disodium (EDTA); and water. This solution has a pH between 3 and 6.5, exhibits 0.2% or less of phenylephrine impurities after exposure to a temperature of 40° C. for a period of 6 months, and optionally consists of one or more of a preservative, buffer or pH adjuster. A most preferred solution has phenylephrine hydrochloride in an amount of about 0.1 mg/mL; sodium chloride in an amount of about 3.64 mg/mL; edetate disodium in an amount of about 0.2 mg; and water, with the solution having a pH of from 5 to 5.3. This solution may include one or more of benzyl alcohol in an amount of about 8 mg/mL, a citrate buffering system of for assisting in maintaining the pH of the solution, and/or hydrochloric acid, sodium hydroxide or both for pH adjustment, if necessary.

The invention also relates to a sterile liquid pharmaceutical product that includes one of the solutions disclosed herein packaged into a container or vial for injection, the container or vial having less than 10% by volume oxygen content in the head space. The solution is preferably present in the container or vial in an amount of 0.05 to 20 mL and the head space has an oxygen content of less than 5% by volume. Advantageously, the solution is present in an amount that allows only a single use of the container or vial.

The invention also relates to a method for making the stable, ready-to-use injection solutions disclosed herein, which comprises admixing from about 0.05 mg/mL to about 0.15 mg/mL phenylephrine hydrochloride; from about 3 mg/mL to about 4 mg/mL of sodium chloride; from about 0.1 mg/mL to about 0.3 mg/mL of edetate disodium; and water for injection q.s. to form the stable, ready-to-use injection solution. About 0.05 to about 20 mL of the solution may be filled in a container or vial, the container is sterilized at a temperature of 120° C.; and the sterilized container or vial is aseptically sealed. The method provides the head space of the container or vial with an oxygen content that is below 10% and preferably below 5% by volume. This is provided by adding nitrogen to the container or vial. Also, the amount of the solution is provided to allow only a single use of the container or vial.

Additional embodiments and advantages of the invention will be set forth in part in the description which follows, and in part will be obvious from the description, or may be learned by practice of the invention. The embodiments and advantages of the invention will be realized and attained by means of the elements and combinations particularly pointed out in the appended claims. It is to be understood that both the foregoing general description and the following detailed description are exemplary and explanatory only and are not restrictive of the invention as claimed.

DETAILED DESCRIPTION OF THE INVENTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures and, or, formulation details have been described at a relatively high-level, without detail, in order to avoid unnecessarily obscuring aspects of the present teachings.

The invention may be more fully understood by reference to the following definitions.

When the singular forms "a," "an" and "the" or like terms are used herein, they will be understood to include plural referents unless the context clearly dictates otherwise. Thus, for example, reference to "a pharmaceutical carrier" includes mixtures of two or more such carriers, and the like. The word "or" and like terms mean any one member of a particular list and also includes any combination of members of that list.

When used herein the term "about" will compensate for variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product. Alternatively, the term can allow for up to 5, 10, 15 or 20% variation from the stated value. Where particular values are described in the application and claims, unless otherwise stated, the term "about" is implicit and in this context means within an acceptable error range for the particular value.

Throughout the description and claims of this specification, the word "comprise" and variations of the word, such as "comprising" and "comprises," means "including but not limited to," and is not intended to exclude, for example, other additives, components, integers or steps. The term "consisting essentially of" means that other additives or components that impart a material change to the invention are not encompassed by the claims. For example, a stable formulation consisting essentially of recited components would exclude other additives that are conventionally used for imparting stability or anti-oxidation properties to the formulation, as these additives are not needed based on the components that are specifically recited to be present.

When ranges are given by specifying the lower end of a range separately from the upper end of the range, it will be understood that the range can be defined by selectively combining any one of the lower end variables with any one of the upper end variables that is mathematically possible.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts that are pharmaceutically acceptable, as defined above, and that possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

Preferably, the phenylephrine salt is phenylephrine hydrochloride.

The term "pharmaceutical solution" or "solution" refers to a mixture with a suitable pharmaceutical excipient, diluent or carrier selected with regard to the intended route of administration and standard pharmaceutical practice. The excipient, diluent and/or carrier must be "acceptable" in the sense of being compatible with the other ingredients of the solution and not deleterious to the recipient thereof. Acceptable excipients, diluents, and carriers for therapeutic use are well known in the pharmaceutical art, and are described, for example, in Remington: The Science and Practice of Pharmacy, Lippincott Williams & Wilkins (A. R. Gennaro edit. 2005). The choice of pharmaceutical excipient, diluent, and carrier can be selected with regard to the intended route of administration and standard pharmaceutical practice. The most preferred excipients, diluents and carriers are disclosed herein and in the examples.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

The present formulations are designated as "stable" if they provide the same or less total impurities when exposed to a wider range of system parameters, i.e., oxygen head space, pH, and temperature. In particular, the stable formulations of the present invention have been found to exhibit 0.2% or less, 0.15% or less and preferably 0.1% or less of total phenylephrine impurities. As a skilled artisan would know, "phenylephrine impurities" refers to impurities that are oxidative or other degradation products of phenylephrine that can cause precipitates or discoloration of the phenylephrine solutions. Thus, the inventive formulations meet the reporting requirement for such impurities of 0.1% or less, with no need for a particular identification or qualification of such impurities as they are present at an amount of 0.2% or less.

These compositions can also contain preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

The concentration of drug may be adjusted, the pH of the solution buffered and the isotonicity adjusted to be compatible with intravenous injection, as is well known in the art.

A citrate buffer can be in the form of citric acid and/or a salt of citric acid.

As noted herein, the invention provides a dilute, ready-to-use sterile injection solution of phenylephrine hydrochloride having improved stability and utility over the prior art. This ready-to-use solution of phenylephrine hydrochloride consists essentially of 0.05 mg/mL to about 0.15 mg/mL phenylephrine hydrochloride as the sole active agent in the solution, 3 mg/mL to about 4 mg/mL of sodium chloride, 0.1 mg/mL to about 0.3 mg/mL of edetate disodium (EDTA) and water for injection (WFI) with the option of adding preservatives. Notably, this invention is free of any sodium metabisulfite antioxidants yet is not prone to destabilization. Instead, the solution includes very small amounts of the chelating agent, EDTA, through which a stable formulation was produced.

The current invention embodies the following:
  a ready-to-use, stable solution of phenylephrine hydrochloride;
  a form for injection that includes the solution packaged in a single-use container with less than ten percent oxygen content in the head space of the container;
  a method to make the injectable solution for use in the single-use container;
  a form for containing the ready-to-use solution that includes a sterile, sealed container holding therein approximately 0.05 to 20 mL of the solution; and
  a method for making the ready-to-use solution for containment in the sterile, sealed container.

Sodium metabisulfite is an effective antioxidant in currently marketed 10 mg/mL solutions of phenylephrine hydrochloride, and prevents unwanted oxidation of the active ingredient. In the present invention, however, when used in more dilute solutions of phenylephrine hydrochloride such as those needed to for ready-to-use, sodium metabisulfite actually destabilizes the formulation. Thus, sodium metabisulfite is specifically excluded from the present solutions due to this detrimental effect.

In the course of developing dilute, stable ready-to-use ("RTU") formulations of phenylephrine hydrochloride, it has unexpectedly been discovered that conventional antioxidants, such as sodium metabisulfite—which stabilize the formulation when used in the prior art concentrated formulations—do not protect the formulation from oxidation in more dilute RTU formulations, but actually destabilize the formulation. A stable formulation could not be manufactured simply by diluting the currently marketed sodium metabisulfite 10 mg/mL solution to a ready-to-use concentration.

In contrast, it has unexpectedly been discovered that when a chelating agent such as edetate disodium (EDTA) is used in relatively low amounts of 0.1 to 0.3 mg/ml, in place of a conventional antioxidant, the stability problems of such solutions are resolved. Instead, the resulting lower concentration solutions are more stable during shelf life. Also, the formulation is stable over a wide range of temperatures, oxygen exposure and a defined pH range.

In particular, it was unexpectedly found that when the conventional antioxidant sodium metabisulfite was replaced with a chelating agent such as EDTA, the resulting formulation was stable. This is a very surprising finding in view of the fact that the prior art discloses that antioxidants are necessary and further because antioxidants and chelating agents work via different mechanisms. While antioxidants typically work by competing for oxidizing species, chelating agents function by sequestering metals that might catalyze unwanted reactions. Thus, if a chelating agent was needed in the formulation, one would have expected to discover this need in the prior art concentrated formulations since those formulations include the same ingredients as the current RTU formulation, but in greater concentrations. Nonetheless, use of a chelating agent in place of a conventional antioxidant such as sodium metabisulfite provides a RTU formulation having greater stability and utility.

Therefore, the present invention provides a RTU solution of phenylephrine hydrochloride that ranges from 0.05 mg/mL to about 0.15 mg/mL phenylephrine hydrochloride as the sole active agent in the solution, 3 mg/mL to about 4 mg/mL of sodium chloride, 0.1 mg/mL to about 0.3 mg/mL of EDTA and water. Notably, the RTU solution of the present invention is free of bisulfites or any other antioxidants and further consists essentially of one or more of a preservative, a chelating agent and/or a pH adjustor. Furthermore, the invention provides a form for injection of the RTU solution whereby the solution is packaged in a single-use container for injection with less than ten percent oxygen content in the head space, as well as a method to make the injectable solution for use in the single-use container. Still furthermore, the invention provides a form for containing the RTU solution that includes a sterile, sealed container holding therein approximately 0.05 to 20 mL of the solution, as well as a method for making the RTU solution for containment in the sterile, sealed container.

Another embodiment of the invention is a RTU solution of phenylephrine hydrochloride that consists essentially of from about 0.05 mg/mL to about 0.15 mg/mL phenylephrine hydrochloride; from about 3.0 mg/mL to about 4.0 mg/mL of sodium chloride; from about 0.1 mg/mL to about 0.3 mg/mL of EDTA; and water. This solution does not contain any bisulfites or other antioxidants and further consists essentially of one or more of a preservative, chelating agent and/or a pH adjustor.

Thus, in a further embodiment, the invention provides a RTU solution of phenylephrine hydrochloride consisting of: from about 0.05 mg/mL to about 0.15 mg/mL phenylephrine hydrochloride as the sole active agent in the solution; from about 3 mg/mL to about 4 mg/mL of sodium chloride; from about 0.1 mg/mL to about 0.3 mg/mL of edetate disodium (EDTA); and water, with the solution optionally consisting of one or more of a preservative, chelating agent and/or pH adjuster. If the preservative is present, it is preferably benzyl alcohol. Additionally, if the chelating agent is present, it is a citrate buffering system for assisting in maintaining the pH of the solution. Finally, if the pH adjuster is present, it is preferably hydrochloric acid or sodium hydroxide or both.

In a more particular embodiment, the invention provides a RTU solution of about 0.1 mg/mL phenylephrine hydrochloride, about 3.64 mg/mL sodium chloride, about 0.2 mg/mL EDTA and water, with the solution having a pH from 3 to 6.5 and preferably from 5 to 5.75. This solution may also include a preservative of about 8 mg/mL benzyl alcohol; a chelating agent of a citrate buffering system for assisting in maintaining the pH of the solution; and/or a pH adjustor that is hydrochloric acid, sodium hydroxide or both, if necessary.

In yet another embodiment the invention, a RTU injection isotonic solution of phenylephrine hydrochloride is provided, that includes from about 0.05 mg/mL to about 0.15 mg/mL phenylephrine hydrochloride, a tonicity agent, a chelating agent, preferably of EDTA, a pH buffering agent and water.

In any of the foregoing embodiments, the solution may be present in a container such as an ampule, vial or bag. The container will preferably comprise from about 0.5 to about 20 mL of solution, but most preferably will comprise about 1.3 mL of solution, yielding a product labeled as a 1.0 mL product.

Another embodiment of the invention relates to a method of making a RTU injection solution of phenylephrine hydrochloride by admixing from about 0.05 mg/mL to about 0.15 mg/mL phenylephrine hydrochloride; from about 3.0 mg/mL to about 4.0 mg/mL of sodium chloride; from about 0.1 mg/mL to about 0.3 mg/mL of EDTA; and water to form the RTU injection solution. The method then calls for filling a container or vial with about 0.5 to about 20 mL of the solution; and sealing the container or vial. In a more preferred embodiment, the method comprises admixing about 0.1 mg/mL phenylephrine hydrochloride, about 3.64 mg/mL sodium chloride; about 0.2 mg/mL of edetate disodium, and water to form the ready-to-use injection solution. The method of this embodiment then calls for filling a container or vial with about 1.3 mL of the solution, and sterilizing and sealing the container.

After admixing the RTU injection solutions disclosed herein, filling the container or vial, and sterilizing and sealing the container or vial, the invention calls for providing a headspace in the sealed container or vial consisting of less than 10% by volume of oxygen content and preferably below 5% by volume by adding nitrogen to the container or vial.

The invention also relates to ready-to-use injection solutions of phenylephrine hydrochloride made by any of the manufacturing processes disclosed herein.

In any of the foregoing embodiments, the solution can have a pH from 3 to 6.5. In particular, the solution will have a preferred pH from 4 to 6. And, even more preferably, a pH that ranges from 5 to 5.75 is often used. Finally, and most preferably, a pH that ranges from 5 to 5.3 is believed to be optimum. Alternatively or in addition, in any of the foregoing embodiments, the solution can comprise a pH adjuster to achieve the desired pH values. There are many examples to those of skill in the art of suitable solutions to adjust the pH of a solution. Two exemplary solutions, as stated above, are sodium hydroxide and hydrochloric acid solution, either of which (or both) should preferably be used to adjust the pH of the solution.

In yet another embodiment, the solution is manufactured via terminal sterilization after the final filling step. The terminal sterilization can be conducted by exposing the sealed container to a temperature in excess of 120 degrees Celsius.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1 is a comparative example of the currently marketed solution containing a sodium metabisulfite antioxidant evaluated at lower strengths. Examples 2 and 3 exemplify the present invention, and evaluate the solutions, unpreserved and preserved, respectively, when the antioxidant is replaced by a chelating agent—namely, EDTA. Example 4 displays a comparison between the solutions of Examples 1 and 2 to show the improved stability by using the chelating agent in place of the antioxidant. Example 5 displays the differences in stability in solutions disclosed in the prior art '691 patent to demonstrate that solutions containing EDTA that maintain a pH of approximately 5 to 5.3 are unexpectedly more stable than such solutions at higher, as well as lower, pH values. Example 6 provides additional stability studies of the preferred formulations of the invention.

Example 1: Diluted Version of Currently Marketed Concentrate Formulation

A diluted version of the currently marketed 10 mg/mL commercial formulation was prepared by adding $\frac{1}{100}^{th}$ or $\frac{1}{200}^{th}$ the quantity of phenylephrine hydrochloride, while keeping the quantities of the other ingredients constant.

TABLE 1

Formulation A - Phenylephrine HCl Injection, 0.1 or 0.05 mg/ml
(Current Formulation Diluted to 0.1 or 0.05 mg/ml)

| Formulation | Raw Material | Amount per mL |
|---|---|---|
| Active | Phenylephrine HCl, USP | 0.1 mg OR 0.05 mg |
| Tonicity Adjuster | Sodium Chloride, USP | 3.5 mg |
| Buffering Agent | Citric Acid, Monohydrate | 1.0 mg |
| Buffering Agent | Sodium Citrate Dihydrate, USP | 4.0 mg |
| Antioxidant | Sodium Metabisulfite, NF | 2.0 mg |
| pH Adjuster | Hydrochloric Acid Sodium Hydroxide | As required to adjust pH |
| Vehicle | WFI | QS to 100% |
| Excipient | Nitrogen, NF | As Needed |

Example 2: Solution of the Current Invention

A diluted version of the currently marketed 10 mg/mL commercial formulation was prepared by adding $\frac{1}{100}^{th}$ or $\frac{1}{200}^{th}$ the quantity of phenylephrine hydrochloride, while keeping the quantities of the other ingredients constant. In addition, a chelating agent (EDTA disodium) was used in place of the antioxidant sodium metabisulfite.

TABLE 2

Formulation B - Phenylephrine HCl Injection, 0.1 mg/ml
(Inventive Formulation - Unpreserved)

| Formulation | Raw Material | Amount per mL |
|---|---|---|
| Active | Phenylephrine HCl, USP | 0.1 mg OR 0.05 mg |
| Tonicity Adjuster | Sodium Chloride, USP | 3.64 mg |
| Buffering Agent | Citric Acid, Monohydrate | 1.0 mg |
| Buffering Agent | Sodium Citrate Dihydrate, USP | 4.0 mg |
| Chelating Agent | Edetate Disodium (EDTA) | 0.2 mg |
| pH Adjuster | Hydrochloric Acid Sodium Hydroxide | As required to adjust pH |
| Vehicle | WFI | QS to 100% |
| Excipient | Nitrogen, NF | As Needed |

Example 3: Solution of the Current Invention, Preserved

A different solution of the present invention was also prepared that exhibited exceptional stability. In this example, a diluted version of the currently marketed 10 mg/mL commercial formulation was prepared by adding $\frac{1}{100}^{th}$ or $\frac{1}{200}^{th}$ the quantity of phenylephrine hydrochloride, while keeping the quantities of the other ingredients constant. In addition, a chelating agent (EDTA disodium) was used in place of the antioxidant sodium metabisulfite in an amount of 0.2 mg, and 8 mg. of benzyl alcohol was added as a preservative so that the formulation could be used in multi-dose vials.

TABLE 3

Formulation C - Phenylephrine HCl Injection, 0.1 mg/ml
(Inventive Formulation - Preserved)

| Formulation | Raw Material | Amount per mL |
|---|---|---|
| Active | Phenylephrine HCl, USP | 0.1 mg OR 0.05 mg |
| Tonicity Adjuster | Sodium Chloride, USP | 3.64 mg |
| Buffering Agent | Citric Acid, Monohydrate | 1.0 mg |
| Buffering Agent | Sodium Citrate Dihydrate, USP | 4.0 mg |
| Chelating Agent | Edetate Disodium (EDTA) | 0.2 mg |
| Preservative | Benzyl Alcohol | 8 mg |
| pH Adjuster | Hydrochloric Acid Sodium Hydroxide | As required to adjust pH |
| Vehicle | WFI | QS to 100% |
| Excipient | Nitrogen, NF | As Needed |

Example 4: Stability of Solutions in Examples 1 and 2

Stability studies were undertaken to evaluate the stability of the sodium metabisulfite and EDTA solutions of Examples 1 and 2 respectively, at various conditions of temperature, and at differing pH values, using both aseptic and terminal sterilization (T greater than 120° C.) procedures to sterilize the solution. Results are reported in Tables 4a, 4b and 4c.

TABLE 4a

Formulation Comparison - Total Impurities at 40° C.
Oxygen Headspace = 5%, Terminally Sterilized at $F_0 = 15$

| | Example 1 | | | Example 2 | | |
|---|---|---|---|---|---|---|
| | pH 4.0 | pH 5.0 | pH 6.0 | pH 4.0 | pH 5.0 | pH 6.0 |
| Time Zero | 0.7% | 1.8% | 1.6% | 0.5% | 0.1% | 0.2% |
| 14 days | 0.5% | 1.4% | 1.3% | 0.3% | 0.1% | 0.1% |
| 1 Month | 0.2% | 1.3% | 1.3% | <LOQ | 0.1% | 0.3% |
| 2 Months | 0.8% | 0.9% | 1.4% | 0.3% | 0.1% | 0.7% |
| 3 Months | <LOQ | 1.6% | 1.2% | 0.1% | 0.1% | 0.2% |
| 6 Months | 0.4% | 2.3% | 2.5% | 0.2% | 0.1% | 0.4% |

TABLE 4b

Formulation Comparison - Total Impurities at 40° C.
Oxygen Headspace = 5%, pH 5.1

| | Example 1 | | Example 2 | |
|---|---|---|---|---|
| | Aseptic | Terminal | Aseptic | Terminal |
| Time Zero | 0.7% | 1.8% | 0.1% | 0.1% |
| 14 days | 0.3% | 1.4% | 0.1% | 0.1% |
| 1 Month | 0.2% | 1.3% | 0.1% | 0.1% |
| 2 Months | 0.2% | 0.9% | 0.5% | 0.1% |
| 3 Months | 0.6% | 1.6% | 0.1% | 0.1% |
| 6 Months | 1.7% | 2.3% | 0.1% | 0.1% |

TABLE 4c

Formulation Comparison - Total Impurities at 70° C.
Oxygen Headspace = 5%, pH 5.1

| | Example 1 | | Example 2 | |
|---|---|---|---|---|
| | Aseptic | Terminal | Aseptic | Terminal |
| Time Zero | 0.7% | 1.8% | 0.1% | 0.1% |
| 7 Days | 2.5% | 3.1% | 0.4% | 0.3% |
| 14 Days | 3.6% | 4.4% | 0.1% | 0.1% |
| 21 Days | 4.1% | 4.1% | 0.1% | 0.0% |
| 30 Days | 4.2% | 4.3% | 0.1% | 0.1% |

The results show that sterilized formulations of the present invention are extremely stable and predominantly exhibit total impurities at no more than 0.1% at the times and temperatures tested.

Example 5: Comparative Formulations

Solutions disclosed in US2014/0235691 A1 patent were studied and compared to those of the present invention. The '691 application discloses a dual drug formulation that incorporated a sodium citrate buffer system to maintain the pH between 5.8 to 6.8 with 6.3 as the preferred pH. The two active ingredients in the formulation were ketorolac and phenylephrine. Further, the formulation was described as preservative free and antioxidant free.

The '691 application provided extensive stability data for various formulations at different temperatures and pH values. EDTA was included in several of the formulations at a concentration of 0.05% w/v (or 0.5 mg/ml), and certain of the data directed to the EDTA containing formulations have been extracted and appear in this Example 5.

TABLE 5a

Percent Phenylephrine Impurities
5 mM(1.88 mg/mL) Ketorolac/5 mM(1.02 mg/mL)
Phenylephrine, No Excipients or Additives, at 40° C.

| Time (Months) | pH 7.4 | pH 6.5 | pH 5.5 |
|---|---|---|---|
| 0 | 0.00 | 0.00 | 0.00 |
| 1 | 0.00 | 0.00 | 0.00 |
| 2 | 0.00 | 0.00 | 0.00 |
| 3 | 0.25 | 0.00 | 0.00 |
| 4 | 0.40 | 0.33 | 0.00 |
| 6 | 1.22 | 0.87 | 0.44 |
| 9 | 0.29 | 0.48 | 0.09 |
| 12 | 1.90 | 0.93 | 1.25 |

For this comparative example, the results show unacceptable impurities starting at 3 months for the pH 7.4 formulation, 4 months for the pH 6.5 formulation and 6 months for the pH 5.5. formulation. This suggests that the lower pH formulations exhibit less impurities even without anti-oxidants or EDTA; however, this data is contradicted by other data provided in the '691 application as shown in Table 5b.

TABLE 5b

Percent Phenylephrine Impurities
1 mM(0.38 mg/mL) Ketorolac/1 mM(0.20 mg/mL)
Phenylephrine, pH = 4.5, No Excipients or Additives

| Time (Months) | 2-8° C. | 25° C. | 40° C. | 60° C. |
|---|---|---|---|---|
| 0 | 0.00 | 0.00 | 0.00 | 0.00 |
| 0.5 | 0.00 | 0.00 | 0.16 | 0.70 |
| 1 | 0.00 | 0.00 | 0.00 | 1.06 |
| 2 | 0.15 | 0.13 | 0.82 | 3.09 |

This comparative data in Table 5b illustrates that at a pH of 4.5, unacceptable impurities are found at as early as two months for temperatures of 25° C. or below, with unacceptable impurities found as early as at 0.5 months for tests at 40° C. and 60° C. Thus, no correlation could be established for different pH solutions based on the data of Tables 5a and 5b. The data does show that impurities increase over longer term storage at each temperature.

TABLE 5c

Percent Phenylephrine Impurities
5 mM(1.88 mg/mL) Ketorolac/5 mM(1.02 mg/mL)
Phenylephrine, EDTA at 40° C.

| Time (Months) | pH 7.4 | pH 6.5 | pH 5.5 |
|---|---|---|---|
| 0 | 0.00 | 0.00 | 0.00 |
| 1 | 0.00 | 0.00 | 0.00 |
| 2 | 0.00 | 0.00 | 0.00 |
| 3 | 0.00 | 0.00 | 0.00 |
| 4 | 0.50 | 0.32 | 0.00 |
| 6 | 0.77 | 0.40 | 0.13 |
| 9 | 0.47 | 0.48 | 0.35 |
| 12 | 1.38 | 0.76 | 0.45 |

This Table 5c shows that unacceptable impurities were found starting at 4 months for the pH 7.4 and pH 6.5 formulations and at 6 months for the pH 5.5 formulation.

TABLE 5d

Percent Phenylephrine Impurities
1 mM(0.38 mg/mL) Ketorolac/1 mM(0.20 mg/mL)
Phenylephrine, pH = 4.5, EDTA

| Time (Months) | 2-8° C. | 25° C. | 40° C. | 60° C. |
|---|---|---|---|---|
| 0 | 0.00 | 0.00 | 0.00 | 0.00 |
| 0.5 | 0.00 | 0.09 | 0.00 | 0.42 |
| 1 | 0.00 | 0.00 | 0.00 | 0.52 |
| 2 | 0.14 | 0.00 | 0.68 | 2.34 |

This comparative data in Table 5d illustrates that at a pH of 4.5, unacceptable impurities are found at as early as 0.5 months for temperatures of 25° C. or 40° C., with unacceptable impurities found at 2 months for tests at 2-8° C. and 60° C. Thus, no correlation could be established for different pH solutions based on the data of Tables 5c and 5d for formulations that include EDTA. The data does generally show that impurities increase over longer term storage at each temperature.

Tables 5e and 5f illustrate the data for the preferred pH formulations of the '591 application.

TABLE 5e

Percent Phenylephrine Impurities
1 mM(0.38 mg/mL) Ketorolac/1 mM(0.20 mg/mL) Phenylephrine,
pH = 6.5, No Excipients or Additives, with Nitrogen Overlay

| Time (Months) | 4° C. | 25° C. | 40° C. | 60° C. |
|---|---|---|---|---|
| 0 | 0.00 | 0.00 | 0.00 | 0.00 |
| 0.5 | 0.00 | 0.00 | 0.00 | 0.00 |
| 1 | 0.00 | 0.00 | 0.00 | 0.44 |
| 2 | 0.00 | 0.00 | 0.00 | 0.00 |
| 3 | 0.00 | 0.00 | 0.00 | 0.15 |
| 4 | 0.22 | 0.00 | 0.33 | 0.32 |
| 6 | 0.00 | 0.00 | 0.87 | 3.24 |
| 9 | 0.00 | 0.00 | 0.09 | 4.68 |
| 12 | 1.13 | 0.89 | 2.14 | 7.10 |

TABLE 5f

Percent Phenylephrine Impurities
1 mM(0.38 mg/mL) Ketorolac/1 mM(0.20 mg/mL) Phenylephrine,
pH = 6.5, EDTA and Active, with Nitrogen Overlay

| Time (Months) | 4° C. | 25° C. | 40° C. | 60° C. |
|---|---|---|---|---|
| 0 | 0.00 | 0.00 | 0.00 | 0.00 |
| 0.5 | 0.00 | 0.00 | 0.00 | 0.00 |
| 1 | 0.00 | 0.00 | 0.00 | 0.53 |
| 2 | 0.00 | 0.00 | 0.00 | 0.00 |
| 3 | 0.00 | 0.00 | 0.00 | 0.09 |
| 4 | 0.00 | 0.00 | 0.32 | 1.26 |
| 6 | 0.00 | 0.00 | 0.41 | 1.99 |
| 9 | 0.00 | 0.00 | 0.48 | 1.97 |
| 12 | 0.00 | 0.66 | 2.29 | 4.43 |

The data in Table 5e shows unacceptable impurities at 2 months for 60° C., 4 months for 4° C. and 40° C. and 12 months for 25° C., while in Table 5f, unacceptable impurities were found at 1 month for 60° C., 4 months at 40° C. and 12 months at 25° C. This is most likely why the '591 application concluded that EDTA did not provide any benefit, since the unacceptable impurities were encountered at essentially the same times with or without EDTA in the preferred formulations of the '591 application.

In comparison, Tables 4a, 4b and 4c of the invention illustrate much greater stability and much lower impurities on the order of 0.1% at essentially all temperatures tested.

The data was generated from an HPLC analytical method validated to current standards for accuracy and precision, with a determined limit of quantitation LOQ of 0.05%. Thus, the present invention provides unexpected results for the inventive formulations that contain low levels (0.02%) of EDTA compared to the use of higher levels (0.05%) in the '691 application. The best results of the present invention were found at a pH of approximately 5.1.

Example 6: Additional Stability Studies of Phenylephrine Solutions

An additional phenylephrine solution according to Table 6 was prepared with a phenylephrine hydrochloride concentration of 100 ug/mL as follows:

TABLE 6

Phenylephrine HCl Formulations

| Formulation | Raw Material | Amount per mL |
|---|---|---|
| Active | Phenylephrine HCl, USP | 0.1 mg |
| Tonicity Adjuster | Sodium Chloride, USP | 3.64 mg |
| Buffering Agent | Citric Acid, Monohydrate | 1.0 mg |
| Buffering Agent | Sodium Citrate Dihydrate, USP | 4.0 mg |
| Chelating Agent | Edetate Disodium (EDTA) | 0.2 mg |
| pH Adjuster | Hydrochloric Acid Sodium Hydroxide | As required to adjust pH |
| Vehicle | WFI | QS to 100% |

Samples of the solution of Table 6 were tested at 25° C. and 60% RH for various times after which the total impurity content was measured. Results are as follows:

| Sample | 3 months | 6 months | 9 months | 12 months | 18 months | 24 Months |
|---|---|---|---|---|---|---|
| A | 0.1 | 0.1 | 0.1 | 0.1 | 0.1 | 0.1 |
| B | 0.1 | 0.1 | 0.1 | 0.1 | 0.1 | 0.1 |
| C | 0.1 | 0.1 | 0.1 | 0.1 | 0.1 | 0.1 |

Additional samples of the same solution of Table 6 were tested at 30° C. and 65% RH after which the total impurity content was measured. Results are as follows:

| Sample | 3 months | 6 months | 9 months | 12 months | 18 months | 24 Months |
|---|---|---|---|---|---|---|
| D | 0.1 | 0.1 | 0.1 | 0.1 | 0.1 | 0.1 |
| E | 0.1 | 0.1 | 0.1 | 0.1 | 0.1 | 0.1 |
| F | 0.1 | 0.1 | 0.1 | 0.1 | 0.1 | 0.1 |

Finally, additional samples of the same solution of Table 6 were tested at 40° C. and 75% RH after which the total impurity content was measured. Results are as follows:

| Sample | 1 month | 2 months | 3 months | 6 months |
|---|---|---|---|---|
| G | 0.1 | 0.1 | 0.1 | 0.1 |
| H | 0.1 | 0.1 | 0.1 | 0.1 |
| I | 0.1 | 0.1 | 0.1 | 0.1 |

These data further demonstrate that the solutions according to the invention illustrate much greater stability and much lower impurities that are on the order of 0.1% at essentially all temperatures and relative humidity conditions tested.

All patents, patent applications, publications, test methods, protocols, literature, and other materials cited herein are hereby incorporated by reference in their entireties.

Those skilled in the art will appreciate that the present invention has a wide range of applications and that it fulfills the needs of the prior art described herein and meets the above-stated objects. While there has been shown and described preferred embodiments of the invention, it will be evident to those skilled in the art that various modifications and changes may be made thereto without departing from the spirit and the scope of the invention as set forth in the appended claims and equivalents thereof.

What is claimed is:

1. A stable, ready-to-use sterile intravenous injection solution of phenylephrine hydrochloride packaged into a vial for injection, wherein the solution comprising:
   from about 0.05 mg/mL to about 0.15 mg/mL phenylephrine hydrochloride as the only active pharmaceutical ingredient in the solution;
   from about 0.1 mg/mL to about 0.3 mg/mL of edetate disodium (EDTA);
   sodium chloride; and
   water;
   wherein the solution has a pH between 3 and 6.5, is stored in a single use vial, and exhibits 0.2% or less of phenylephrine impurities after exposure to a temperature of 40° C. for a period of 6 months; and wherein the solution is free of bisulfites or other antioxidants.

2. A stable, ready-to-use sterile intravenous injection solution of phenylephrine hydrochloride packaged into a vial for injection, wherein the solution comprising:
   from about 0.05 mg/mL to about 0.15 mg/mL phenylephrine hydrochloride as the only active pharmaceutical ingredient in the solution;
   from about 0.1 mg/mL to about 0.3 mg/mL of edetate disodium (EDTA);
   one or more of a preservative, a buffer and/or a pH adjustor;
   sodium chloride; and
   water;
   wherein the solution has a pH between 3 and 6.5, is stored in a single use vial, and exhibits 0.2% or less of phenylephrine impurities after exposure to a temperature of 40° C. for a period of 6 months; and
   wherein the solution is free of bisulfites or other antioxidants.

3. The solution of claim 2, wherein the preservative is present and comprises benzyl alcohol, chlorobutanol, paraben, phenol sorbic acid or a combination thereof.

4. The solution of claim 2, wherein the buffer is present and is a citrate buffering system for assisting in maintaining the pH of the solution.

5. The solution of claim 2, wherein the pH adjuster is present and is hydrochloric acid, sodium hydroxide or both.

6. The solution of claim 1 which exhibits about 0.1% or less of phenylephrine impurities after exposure to a temperature of 40° C. for a period of 6 months.

7. The solution of claim 1 which has:
   phenylephrine hydrochloride in an amount of about 0.1 mg/mL; and
   edetate disodium in an amount of about 0.2 mg;
   with the solution having a pH of from 5 to 5.3.

8. The solution of claim 7, wherein one or more of the following are present:
   benzyl alcohol in an amount of about 8 mg/mL,
   a buffering system for assisting in maintaining the pH of the solution, and/or hydrochloric acid, sodium hydroxide or both for pH adjustment, if necessary.

9. A sterile liquid pharmaceutical product that includes a stable, ready-to-use sterile intravenous injection solution of phenylephrine hydrochloride packaged into a vial for injection, the vial having less than 10% by volume oxygen content in a head space of the vial, wherein the solution comprising:
from about 0.05 mg/mL to about 0.15 mg/mL phenylephrine hydrochloride as the only active pharmaceutical ingredient in the solution;
from about 0.1 mg/mL to about 0.3 mg/mL of edetate disodium (EDTA);
sodium chloride; and
water;
wherein the solution has a pH between 3 and 6.5, is stored in a single use vial, and exhibits 0.2% or less of phenylephrine impurities after exposure to a temperature of 40° C. for a period of 6 months; and wherein the solution is free of bisulfites or other antioxidants.

10. The product of claim 9, wherein the solution is present in the vial in an amount of 0.05 to 20 mL and the head space has an oxygen content of less than 5% by volume.

11. The product of claim 9, wherein the solution is present in an amount that allows only a single use of the vial.

12. A method for making the stable, ready-to-use injection solution of phenylephrine hydrochloride according to claim 1, which comprises admixing from about 0.05 mg/mL to about 0.15 mg/mL phenylephrine hydrochloride; from about 0.1 mg/mL to about 0.3 mg/mL of edetate disodium; sodium chloride; and water for injection q.s. to form the stable, ready-to-use injection solution.

13. The method of claim 12 that further comprises filling a vial with from about 0.05 to about 20 mL of the solution.

14. The method of claim 13, which further comprises providing the head space of the vial with an oxygen content that is below 10%.

15. The method of claim 14, wherein the oxygen content of the head space of the vial is below 5% by volume and is provided by adding nitrogen to the vial.

16. The method of claim 13, which further comprises providing an amount of the solution that allows only a single use of the vial.

17. A sterile liquid pharmaceutical product that includes the solution of claim 2 packaged into the vial for injection.

18. The solution of claim 1, which further consists essentially of one or more of a preservative, a buffer and/or a pH adjustor.

19. A stable, ready-to-use sterile intravenous injection solution of phenylephrine hydrochloride packaged into a vial for injection, wherein the solution comprising:
from about 0.05 mg/mL to about 0.15 mg/mL phenylephrine hydrochloride as the only active pharmaceutical ingredient in the solution;
from about 0.1 mg/mL to about 0.3 mg/mL of edetate disodium (EDTA);
sodium chloride; and
water;
wherein the solution is stored in a single use vial and exhibits 0.2% or less of phenylephrine impurities after exposure to a temperature of 40° C. for a period of 6 months; and wherein the solution is free of bisulfites or other antioxidants.

20. The solution of claim 19, wherein the bisulfites comprise sodium metabisulfite.

21. The solution of claim 19, wherein the solution further comprising wetting agents, emulsifying agents, dispersing agents, antibacterial/antifungal agents or a combination thereof.

* * * * *